United States Patent
Kim et al.

(10) Patent No.: US 10,488,414 B2
(45) Date of Patent: Nov. 26, 2019

(54) MULTI-INFLUENZA DETECTION KIT AND METHOD FOR DETECTING INFLUENZA USING THE SAME

(71) Applicant: GREEN CROSS MEDICAL SCIENCE, Yongin-si, Gyeonggi-do (KR)

(72) Inventors: Serka Kim, Eumseong-gun (KR); Woo-Sung Jung, Eumseong-gun (KR); Young-Mi Lee, Yongin-si (KR); Chae Seung Lim, Seoul (KR)

(73) Assignee: GREEN CROSS MEDICAL SCIENCE, Yongin-si (KR)

( * ) Notice: Subject to any disclaimer, the term of this patent is extended or adjusted under 35 U.S.C. 154(b) by 321 days.

(21) Appl. No.: 15/324,564

(22) PCT Filed: Jul. 8, 2015

(86) PCT No.: PCT/KR2015/007033
§ 371 (c)(1),
(2) Date: Jan. 6, 2017

(87) PCT Pub. No.: WO2016/006922
PCT Pub. Date: Jan. 14, 2016

(65) Prior Publication Data
US 2018/0180613 A1    Jun. 28, 2018

(30) Foreign Application Priority Data

Jul. 8, 2014  (KR) .................. 10-2014-0085147

(51) Int. Cl.
*G01N 33/569* (2006.01)
*G01N 33/558* (2006.01)
*G01N 21/78* (2006.01)

(52) U.S. Cl.
CPC ....... *G01N 33/56983* (2013.01); *G01N 21/78* (2013.01); *G01N 33/558* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 2007/0224594 A1 | 9/2007 | Lu et al. | |
| 2008/0199851 A1* | 8/2008 | Egan | ............ B01L 3/5023 435/5 |

(Continued)

FOREIGN PATENT DOCUMENTS

| | | | | |
|---|---|---|---|---|
| CN | 201397332 A | | 2/2010 | |
| CN | 202583207 U | * | 5/2012 | ........... G01N 33/569 |

(Continued)

OTHER PUBLICATIONS

Hytest, "Monoclonal mouse anti-influenza A haemagglutinin H5 Cat.# 3H5N", retrieved from https://shop.hytest.fi/product/influenza-haemagglutinin-h5-antibody on Jun. 6, 2019, four pages.*

(Continued)

*Primary Examiner* — Christine Foster
(74) *Attorney, Agent, or Firm* — Sughrue Mion, PLLC

(57) ABSTRACT

The present invention relates to a multi-influenza detection kit comprising monoclonal antibodies and a method of detecting multiple influenza viruses using the kit. More specifically, the present invention relates to a multi-influenza detection kit comprising monoclonal antibodies that bind specifically to influenza type A, type B, subtype H1, subtype H3 and subtype H5, and to a method of detecting influenza viruses using the kit. The multi-influenza detection kit comprising monoclonal antibodies according to the present invention can simultaneously detect influenza types A and B and subtypes H1, H3 and H5, and thus is useful for the rapid (Continued)

and highly sensitive on-site detection and diagnosis of influenza.

16 Claims, 15 Drawing Sheets

Specification includes a Sequence Listing.

(56) References Cited

U.S. PATENT DOCUMENTS

| | | | | |
|---|---|---|---|---|
| 2009/0142377 A1* | 6/2009 | Gebbink | ............ | A61K 39/0005 424/400 |
| 2010/0267006 A1* | 10/2010 | Namba | .............. | C07K 16/1018 435/5 |

FOREIGN PATENT DOCUMENTS

| | | |
|---|---|---|
| CN | 103336121 A | 10/2013 |
| JP | 2010-261912 A | 11/2010 |
| JP | 2013-174607 A | 9/2013 |
| KR | 10-2011-0096940 A | 8/2011 |
| KR | 10-2012-0028603 A | 3/2012 |

OTHER PUBLICATIONS

Medix Biochemica, "Anti-Influenza A 7307 SPTN-5", Date: Aug. 23, 2017, retrieved from https://www.medixbiochemica.com/wp-content/uploads/2017/08/Anti-Influenza-A-7307-SPTN-5-Product-Specification-v2.pdf on Jun. 6, 2019, two pages.*
Rudikoff et al. "Single amino acid substitution altering antigen-binding specificity" Proc Natl Acad Sci USA 1982 vol. 79 pp. 1979-1983.*
Pascalis et al. ("Grafting of "Abbreviated" Complementarity-Determining Regions Containing Specificity-Determining Residues Essential for Ligand Contact to Engineer a Less Immunogenic Humanized Monoclonal Antibody", The Journal of Immunology (2002) 169, 3076-3084.*
Casset et al. "A peptide mimetic of an anti-CD4 monoclonal antibody by rational design" (2003) BBRC 307, 198-205.*
Van Regenmortel "Molecular dissection of protein antigens and the prediction of epitopes", Chapter 1 in: Laboratory Techniques in Biochemistry and Molecular Biology vol. 19, 1988, pp. 1-39.*
Kyung, machine translation for KR20120028603 as retrieved via EPO Patent Translate on Jan. 9, 2019, 26 pages total.*
Medix, Anti-Influenza B 9901 SPTNZ-5, Date: Jul. 11, 2017, retrieved from https://www.medixbiochemica.com/wp-content/uploads/2017/07/Anti-Influenza-B-9901-SPTNZ-5-Product-Specification-v2.pdf on Jun. 7, 2019, 2 pages.*
Health and Welfare Department of Republic of Korea, "Various influenza can be quickly identified at the same time in the field.", A news release, Press Resources, the Ministry of Health and Welfare, Apr. 18, 2014, 14 pages.
Jin Woo Jang et al., "GENEDIA Multi Influenza Ag Rapid Test for detection and H1, H3, and H5 subtyping of influenza viruses", Journal of Clinical Virology, vol. 73, pp. 42-46, 2015, XP029332332, 6 pages.
European Patent Office; Communication dated Nov. 28, 2017 in counterpart European application No. 15819275.7.
Don C. Wiley, et al., "The Structure and Function of the Hemag-glutinin Membrane Glycoprotein of Influenza Virus", Ann. Rev. Biochem., 1987, pp. 365-394, vol. 56.
G. Kohler, et al., "Continuous cultures of fused cells secreting antibody of predefined specificity", Nature, Aug. 7, 1975, pp. 495-497, vol. 256.
Danuta Kozbor, et al., "The production of monoclonal antibodies from human lymphocytes", Immunology Today, 1983, pp. 72-79, vol. 4, No. 3.
International Searching Authority, International Search Report for PCT/KR2015/007033 dated Jul. 21, 2015 [PCT/ISA/210].

* cited by examiner strip configuration          Device design

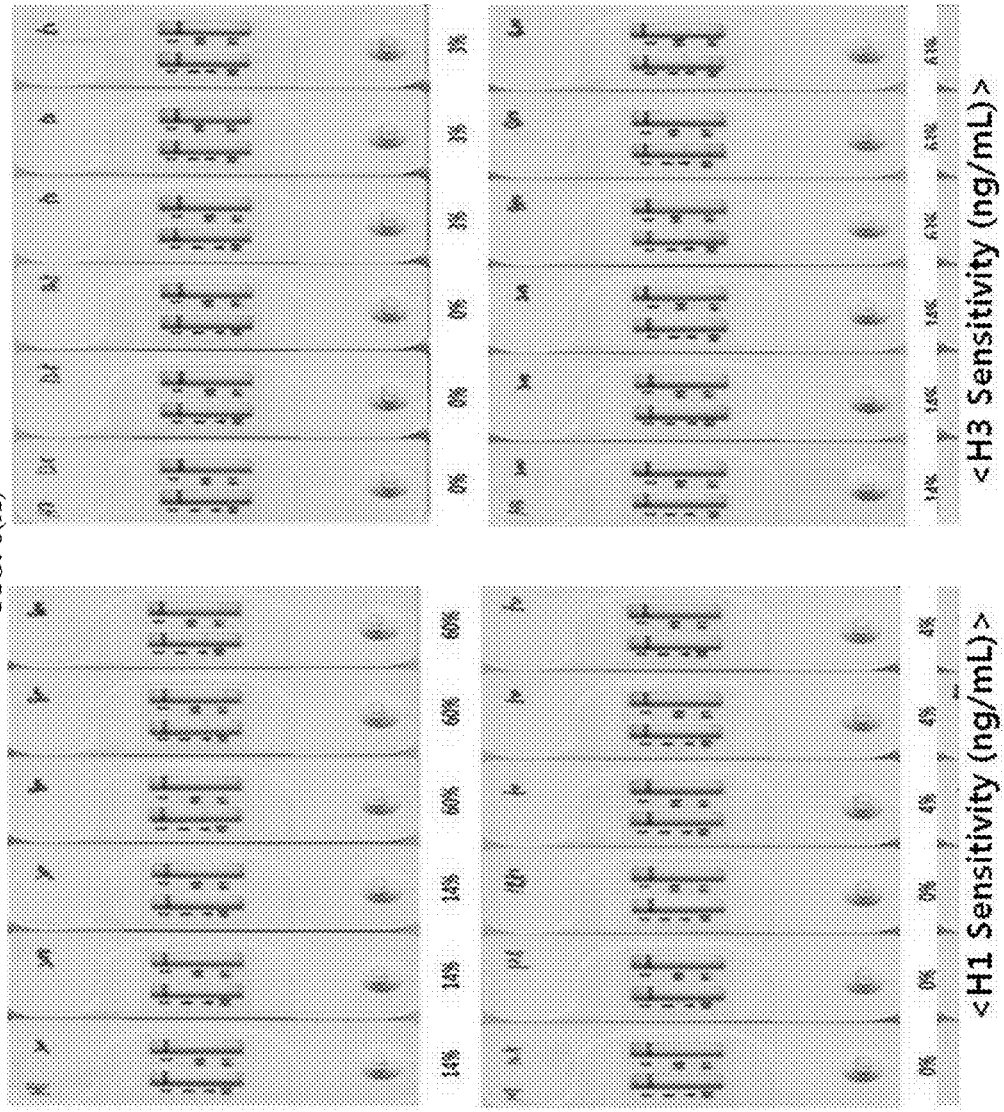

FIG. 6(B)

SEQUENCE LISTING

<160> NUMBER OF SEQ ID NOS: 4

<210> SEQ ID NO 1
<211> LENGTH: 121
<212> TYPE: PRT
<213> ORGANISM: Artificial
<220> FEATURE:
<223> OTHER INFORMATION: SF587 heavy chain variable region

<400> SEQUENCE: 1

```
Val Gln Leu Gln Gln Ser Gly Gly Val Val Gln Pro Gly Gly Ser
1               5                   10                  15

Leu Arg Leu Ser Cys Ala Ala Ser Gly Phe Thr Phe Ser Asp Tyr Asp
            20                  25                  30

Met Ser Trp Ile Arg Gln Ala Pro Gly Lys Gly Leu Glu Trp Val Ser
        35                  40                  45

Gly Ile Leu Gly Gly Gly Glu Arg Ser Tyr Tyr Asn Asp Ser Val Lys
    50                  55                  60

Gly Arg Phe Thr Ile Ser Arg Asp Asn Ser Lys Thr Leu Tyr Leu
65              70                  75                  80

Gln Met Asn Ser Leu Arg Ala Glu Asp Thr Ala Val Tyr Tyr Cys Ala
                85                  90                  95

Arg His Gly Ser Ser Gly Tyr Val Asp Tyr Gly Met Asp Tyr Trp Gly
            100                 105                 110

Gln Gly Thr Thr Val Thr Val Ser Ser
        115                 120
```

<210> SEQ ID NO 2
<211> LENGTH: 109
<212> TYPE: PRT
<213> ORGANISM: Artificial
<220> FEATURE:
<223> OTHER INFORMATION: SF587 light chain variable region

<400> SEQUENCE: 2

```
Asp Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Gly Asp Asn
            20                  25                  30

Leu Gly Trp Tyr Gln Gln Lys Pro Gly Lys Ala Pro Lys Arg Leu Ile
        35                  40                  45

Tyr Gly Val Ser Thr Leu Asp Ser Gly Val Pro Ser Arg Phe Ser Gly
    50                  55                  60

Ser Gly Ser Gly Thr Glu Phe Thr Leu Thr Ile Asn Ser Leu Gln Pro
65              70                  75                  80

Glu Asp Phe Ala Thr Tyr Tyr Cys Leu Gln His Ser Asn Tyr Pro Met
                85                  90                  95

Tyr Thr Phe Gly Gln Gly Thr Lys Leu Glu Ile Lys Arg
            100                 105
```

<210> SEQ ID NO 3
<211> LENGTH: 121
<212> TYPE: PRT
<213> ORGANISM: Artificial
<220> FEATURE:
<223> OTHER INFORMATION: SF757 heavy chain variable region

<400> SEQUENCE: 3

```
Val Lys Leu Gln Glu Ser Gly Gly Val Val Gln Pro Gly Gly Ser
1               5                   10                  15
```

```
Leu Arg Leu Ser Cys Ala Ala Ser Gly Phe Thr Phe Ser Asp Tyr Asp
            20                  25                  30

Met Ser Trp Ile Arg Gln Ala Pro Gly Lys Gly Leu Glu Trp Val Ser
        35                  40                  45

Gly Ile Leu Gly Gly Ser Glu Arg Ser Tyr Tyr Arg Asp Ser Val Lys
50                          55                  60

Gly Arg Ser Thr Ile Ser Arg Asp Asn Ser Arg Lys Thr Leu Tyr Leu
65                      70                  75                  80

Gln Met Asn Ser Leu Arg Ala Glu Asp Thr Ala Val Tyr Tyr Cys Ala
                85                  90                  95

Arg His Ser Trp Gly Ala Tyr Val Gln Tyr Gly Met Asp Val Trp Gly
            100                 105                 110

Gln Gly Thr Thr Val Thr Val Ser Ser
        115                 120

<210> SEQ ID NO 4
<211> LENGTH: 112
<212> TYPE: PRT
<213> ORGANISM: Artificial
<220> FEATURE:
<223> OTHER INFORMATION: SF757 light chain variable region

<400> SEQUENCE: 4

Asp Ile Gln Met Thr Gln Ser Pro Ala Ser Leu Ala Val Ser Pro Gly
1               5                   10                  15

Gln Arg Ala Thr Ile Thr Cys Arg Ala Ser Glu Ser Val Ser Asn Tyr
            20                  25                  30

Gly Ile Asn Phe Ile Asn Trp Phe Gln Gln Lys Pro Gly Gln Pro Pro
        35                  40                  45

Lys Leu Leu Ile Tyr Thr Ala Ser Asn Lys Gly Thr Gly Val Pro Ala
50                      55                  60

Arg Phe Ser Gly Ser Gly Ser Gly Thr Asp Phe Thr Leu Thr Ile Asn
65                  70                      75                  80

Pro Val Glu Ala Glu Asp Thr Ala Asn Tyr Phe Cys Gln Gln Thr Lys
                85                  90                  95

Glu Val Pro Tyr Thr Phe Gly Gly Gly Thr Lys Leu Glu Ile Lys Arg
            100                 105                 110
```

MULTI-INFLUENZA DETECTION KIT AND METHOD FOR DETECTING INFLUENZA USING THE SAME

CROSS REFERENCE TO RELATED APPLICATIONS

This application is a National Stage of International Application No. PCT/KR2015/007033, filed on Jul. 8, 2015, which claims priority from Korean Patent Application No. 10-2014-0085147, filed on Jul. 8, 2014, the contents of all of which are incorporated herein by reference in their entirety.

TECHNICAL FIELD

The present invention relates to a multi-influenza detection kit and a method of detecting multiple influenza viruses using the kit. More specifically, the present invention relates to a multi-influenza detection kit comprising monoclonal antibodies that bind specifically to influenza type A, type B, subtype H1, subtype H3 and subtype H5, and to a method of detecting influenza viruses using the kit.

BACKGROUND ART

Influenza viruses are pathogens that cause viral respiratory disease, and are largely classified into types A, B and C based on the antigenic differences in their NP (nucleocapsid) and M (matrix) proteins. Among them, type A is further classified into subtypes H1 to H15 based on the antigenicity of their HA (hemagglutinin) proteins, and into subtypes N1 to N9 based on their antigenic characteristics of their NA proteins (see Wiely DC and Skehel TT, Ann Rev Biochem, 56:365-394, 1987). Among them, subtypes H1, H2, H3, N1 and N2 generally cause disease in humans. The H and N antigens that appear in birds generally do not cause disease in humans, but can change to types that cause disease even in humans, when genetic mutations in the viruses occur or when the viruses exchange genes with antigens that cause disease in humans. If such new influenza viruses against which humans have no prior immunity emerge, they can cause a worldwide pandemic.

In recent years, various diagnostic kits for detecting such influenza viruses have been developed. In particular, as the number of deaths caused by highly pathogenic avian influenza viruses such as swine influenza has increased rapidly, rapid diagnostic kits for early diagnosis have been required. In the case of diseases (such as a novel swine influenza pandemic in 2009) that spread to many and unspecified persons in public places such as schools and work sites, the quarantine of early infected persons upon diagnosis is required to prevent pandemic, and rapid and accurate early detection systems are required. Such systems are national public systems necessary for public safety. Rapid diagnostic systems for on-site diagnosis should be small in size so as to be easy to carry, should be simple to use, and should provide a user interface so as to be easily operated by the user.

Three main conventional methods used to diagnose influenza are virus culture test, rapid antigen test, and PCR test. Among these methods, the virus culture method that is a traditional diagnosis method is accurate, but has limitations in that it is time-consuming and complicated, and thus provides diagnostic results at a late time. Also, it cannot be applied for treatment. In addition, the rapid antigen test based on antigen-antibody reactions for primary identification of influenza-infected persons is a convenient and rapid test that requires a time of about 30 minutes, and has an advantage in that it does not require an additional system and technical manpower for the test. However, the rapid antigen test has a disadvantage in that, because it detects only the nucleoprotein of types A and B, it has low sensitivity and accuracy, and thus can cause a wrong diagnosis leading to the death of the patient. Thus, it is difficult to apply for on-site diagnosis. The diagnosis of influenza subtypes becomes an index enabling prediction of resistance to influenza treatment drugs, and indicates epidemiologically significant disease prevalence. Currently, the diagnosis of influenza subtypes is possible only by RT-PCR and is costly, and a H1/A/B diagnostic reagent (SD Co., Ltd.) is the only reagent for rapid diagnosis of antigen, which enables the identification of subtypes of type A, and other reagents have not been developed and used worldwide.

Real-time PCR that has been used as a diagnostic test for swine influenza is the most effective mean for diagnosis of infectious diseases due to its high sensitivity and accuracy. However, it requires a test time of 2-4 hours, and may not be used for on-site diagnosis. For these reasons, when performed by a professional organization, a time of about 2-3 days is generally required for confirming the test result. In addition, it is costly. Thus, this real-time PCR cannot be used as an initial countermeasure in a national scope at a time point at which an infectious disease pandemic is expected. Furthermore, avian influenza infecting various kinds of birds, including chickens, turkeys and wild birds, as well as humans, spreads rapidly with diverse pathogenicities. Thus, the infected birds are killed in most of countries in the world in case highly pathogenic avian influenza occurs. Also, a country in which the highly pathogenic avian influenza has occurred is seriously damaged, because it cannot export chicken products.

Accordingly, the present inventors have made extensive efforts to solve the above-described problems, and as a result, have developed an influenza detection kit capable of not only detecting the nucleoproteins of influenza types A/B, but also simultaneously detecting the hemagglutinins of influenza subtypes H1, H3 and H5 without cross reactions, and have found that the use of the developed influenza detection kit enables the on-site detection and diagnosis of even influenza subtypes, including avian influenza subtype H5, thereby completing the present invention.

DISCLOSURE OF INVENTION

Technical Problem

It is an object of the present invention to provide a multi-influenza detection kit capable of detecting influenza subtypes H1, H3 and H5 simultaneously in addition to influenza types A and B.

Another object of the present invention is to provide a method of detecting influenza using the multi-influenza detection kit.

Technical Solution

To achieve the above objects, the present invention provides a multi-influenza detection kit comprising a first strip and a second strip, wherein each of the first strip and the second strip comprises a sample pad, a conjugate pad, a signal pad and an absorbent pad, wherein the conjugate pad and the signal pad of the first strip comprise monoclonal antibodies capable of binding specifically to influenza subtype H3, influenza type A and influenza type B, respectively, and wherein the conjugate pad and signal pad of the second strip comprise monoclonal antibodies capable of binding specifically to influenza subtype H1 and influenza subtype H5, respectively.

The present invention also provides a method of detecting influenza using the multi-influenza detection kit.

BRIEF DESCRIPTION OF THE DRAWINGS

In FIG. 1, strip A and strip B mean a first strip and a second strip, respectively.

In FIG. 3, strip A and strip B mean a first strip and a second strip, respectively.

FIGS. 6(A)-6(C) depict photographs of influenza detection kits, which show sensitivities as a function of the concentrations of multiple influenza antigens.

BEST MODE FOR CARRYING OUT THE INVENTION

Figure 1:
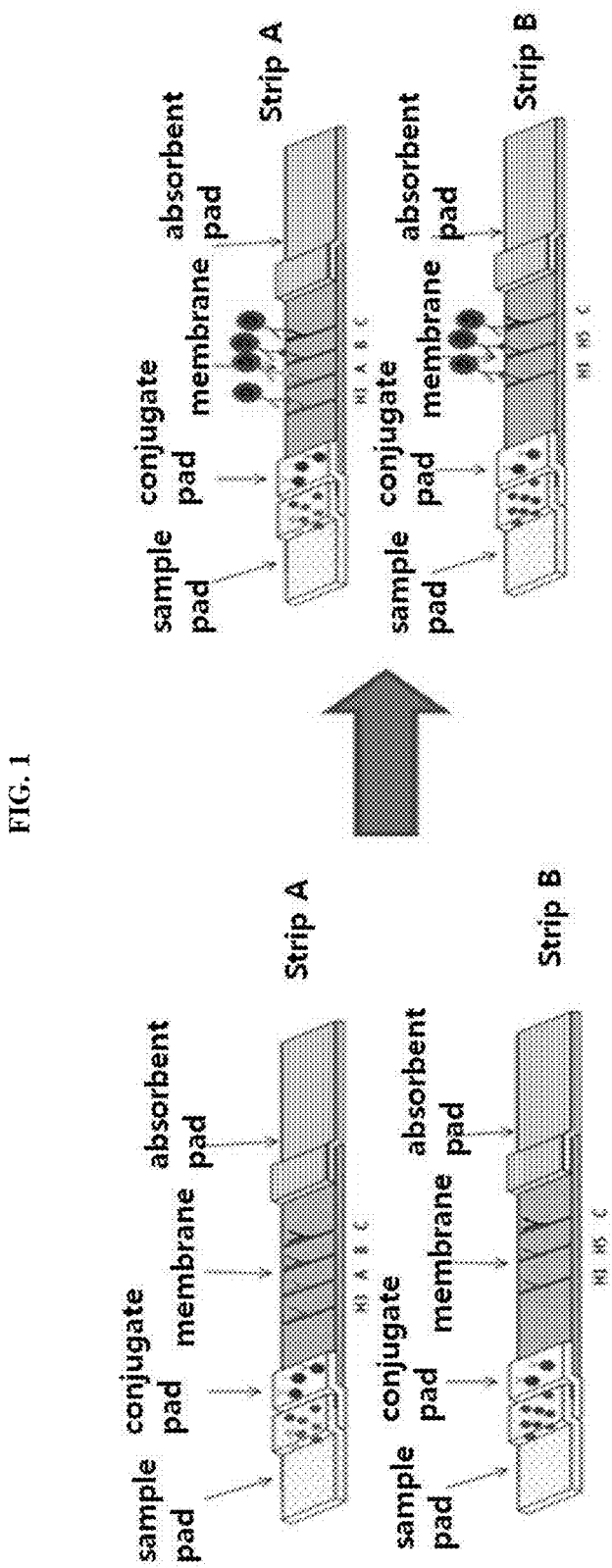
FIG. 1 shows the fundamental principle of a multi-influenza antigen diagnosis system.

Unless otherwise defined, all technical and scientific terms used herein have the same meaning as commonly understood by one of ordinary skill in the art to which the invention pertains. Generally, the nomenclature used herein are well known and commonly used in the art.

In the present invention, an influenza detection kit was prepared which comprises: a first strip comprising monoclonal antibodies that bind specifically to influenza subtype H3, influenza type A and influenza type B; and a second strip comprising monoclonal antibodies that bind specifically to influenza subtype H1 and influenza subtype H5. In order to examine whether the influenza detection kit can effectively detect even influenza A subtypes H1, H3 and H5, the sensitivity and specificity of the kit were evaluated, and the cross-reaction tests were performed. As a result, it was found that the influenza detection kit of the present invention has higher sensitivity compared to that of a kit of other company, which can detect only types A and B, and that it can effectively detect even subtypes H1, H3 and H5.

Thus, in one aspect, the present invention is directed to a multi-influenza detection kit comprising a first strip and a second strip, wherein each of the first strip and the second strip comprises a sample pad, a conjugate pad, a signal pad and an absorbent pad, wherein the conjugate pad and the signal pad of the first strip comprise monoclonal antibodies capable of binding specifically to influenza subtype H3, influenza type A and influenza type B, respectively, and wherein the conjugate pad and signal pad of the second strip comprise monoclonal antibodies capable of binding specifically to influenza subtype H1 and influenza subtype H5, respectively.

In the present invention, the monoclonal antibody, which is included in the conjugate pad and the signal pad of the first strip and binds specifically to influenza subtype H3, may be a monoclonal antibody that binds specifically to the hemagglutinin of influenza subtype H3; the monoclonal antibody that binds specifically to influenza type A may be a monoclonal antibody that binds specifically to the nucleoprotein of influenza type A; and the monoclonal antibody that binds specifically to influenza type B may be a monoclonal antibody that binds specifically to the nucleoprotein of influenza type B.

In addition, the monoclonal antibody, which is included in the conjugate pad and signal pad of the second strip and binds specifically to influenza subtype H1, may be a monoclonal antibody that binds specifically to the hemagglutinin of influenza subtype H1; and the monoclonal antibody that binds specifically to influenza subtype H5 may be a monoclonal antibody that binds specifically to the hemagglutinin of influenza subtype H5.

In the present invention, the conjugate pad of the first strip may comprise: monoclonal antibody NCCP. 76024 that binds specifically to the hemagglutinin of influenza subtype H3; monoclonal antibody 7307 SPTN-5 that binds specifically to the nucleoprotein of influenza type A; and monoclonal antibody 9901 SPTNE-10 that binds specifically to the nucleoprotein of influenza type B.

In addition, the signal pad of the first strip may comprise: monoclonal antibody NCCP. 76024 that binds specifically to the hemagglutinin of influenza subtype H3; monoclonal antibody A60010044P that binds specifically to the nucleoprotein of influenza type A; and monoclonal antibody 10-I55B that binds specifically to the nucleoprotein of influenza type B.

In the present invention, the conjugate pad of the second strip may comprise: a monoclonal antibody that binds specifically to the hemagglutinin of influenza subtype H1 and contains a heavy-chain variable region comprising an amino acid sequence of SEQ ID NO: 1 or 3 and a light-chain variable region comprising an amino acid sequence of SEQ ID NO: 2 or 4; and monoclonal antibody 3H5N-15A6 that binds specifically to the nucleoprotein of influenza subtype H5.

In addition, the signal pad of the second strip may comprise: a monoclonal antibody that binds specifically to the hemagglutinin of influenza subtype H1 and contains a heavy-chain variable region comprising an amino acid sequence of SEQ ID NO: 1 or 3 and a light-chain variable region comprising an amino acid sequence of SEQ ID NO: 2 or 4; and monoclonal antibody 3H5N-15A6 that binds specifically to the nucleoprotein of influenza subtype H5.

The influenza detection kit according to the present invention comprises a first strip and a second strip, in which each of the first strip and the second strip comprises an assembly of a sample pad, a conjugate pad, a signal pad and an absorbent pad. The sample pad functions to quickly absorb the sample (serum, blood or saliva) to be analyzed; the conjugate pad functions to deposit a conjugate of colored colloidal gold and an antibody to visually detect a signal; the signal pad functions to immobilize an antibody by a physical adsorption method so that a signal appears after an antigen-antibody reaction; and the absorbent pad functions to provide a driving force so that a sample is developed upward by capillary action after being added.

Influenza viruses are classified into influenza types A, B and C based on the antigenicity of their soluble nucleoprotein (NP). Influenza type A is further classified into subtypes H and N based on the antigenicity of hemagglutinin (HA) and neuraminidase (NA) proteins present on the surface thereof. In an example of the present invention, in order to separately detect each influenza subtype, monoclonal antibodies that bind specifically to different nucleoproteins in the viruses, were used for the detection of influenza types A and B, and monoclonal antibodies that bind specifically to different hemagglutinins on the surfaces of the viruses, were used for the detection of influenza subtypes H1, H3 and H5. As shown in Table 1 of Example 2 below, the monoclonal antibody for subtype H1 was prepared by the present inventors, and the monoclonal antibodies for other types were purchased from the Korea Centers for Disease Control and Prevention, HyTest Ltd., Biospacific, Inc., Fitzgerald Ltd., Medix Ltd., etc., and then introduced into the influenza detection kit of the present invention, but the scope of the present invention is not limited thereto.

In the present invention, the longitudinal axis of the first strip may be arranged in parallel to the longitudinal axis of the second strip; the monoclonal antibodies included in the conjugate pad of the first strip and the second strip may be present as conjugates with a label; and the monoclonal antibodies included in the signal pad may be fixed in the form of test lines. Furthermore, in the present invention, the label conjugated with the monoclonal antibodies included in the conjugate pad may be colloidal gold.

Figure 5:
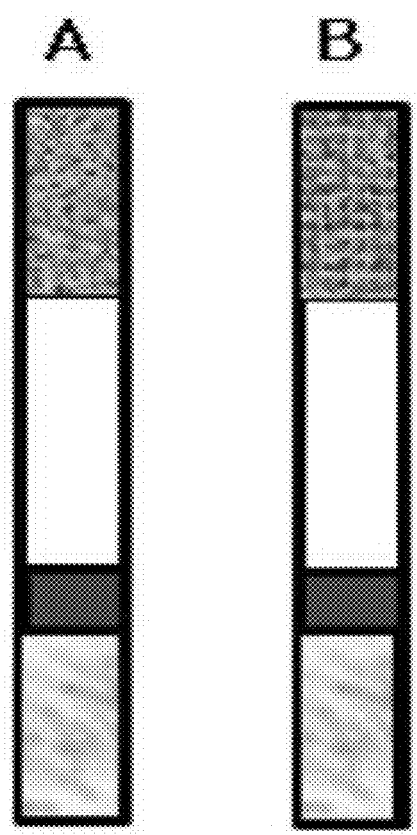
FIG. 5 is a schematic view showing a strip configuration and a device wherein A and B indicate a first strip and a second strip, respectively.
Figure 5:
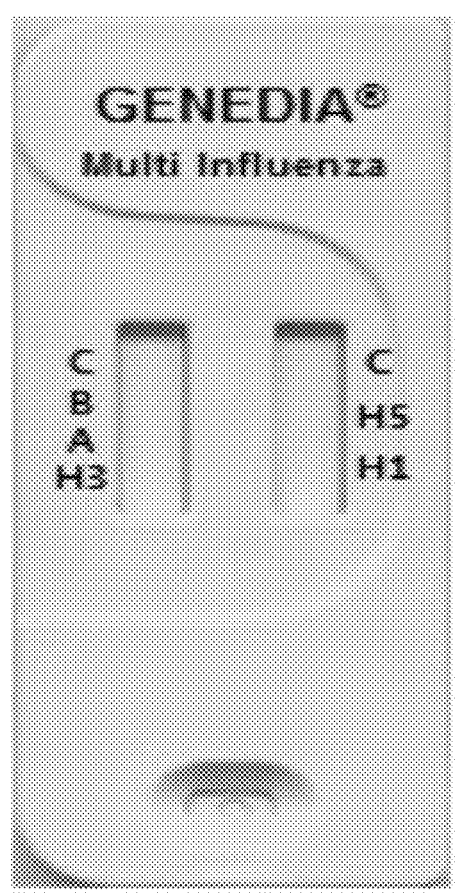

That the longitudinal axis of the first strip is arranged in parallel to the longitudinal axis of the second strip means that the first strip and the second strip are juxtaposed with each other with their longitudinal axes positioned in proximity to each other as shown in FIG. 5. In an example of the present invention, colloidal gold was used as a label that develops a color to emit a signal when an antibody-label conjugate binds to the fixed test line antibody of the signal pad after it did bind to an antigen and moved to the signal pad. In addition to colloidal gold, enzymes may be used, such as horseradish peroxidase, alkaline phosphatase, β-galactosidase, *Arthromyces ramosus* peroxidase, glucose oxidase, urease, penicillin oxidase and cholesterol oxidase. In addition, metal ions such as $Co^{2+}$, $Cu^{2+}$, $Mg^{2+}$ and $Fe^{2+}$ or their compounds may be used. A solution containing a substrate of the enzyme comprises a substrate component for color development, a chemilumigenic component (e.g., luminol), a substrate composition for generating electrochemical signals, or a silver compound, and shows a signal for color development, discoloration, luminescence, a change in electrical conductivity, a change in current or a change in voltage by enzyme-substrate reactions or chemical reactions.

In the present invention, the test lines of the signal pad of the first strip may include an influenza subtype H3 test line, an influenza type A test line and an influenza type B test line, which are fixed in this order from the side close to the sample pad, and the test lines of the signal pad of the second strip may include an influenza subtype H1 test line and an influenza subtype H5 test line, which are fixed in this order from the side close to the sample pad.

In the present invention, the signal pad of each of the first strip and the second strip may further comprise an antibody that binds specifically to mouse antibody C which is used as a control to confirm the development of the sample. Concretely, the antibody that binds specifically to mouse antibody C may be fixed as a test line at the longest distance from the sample pad.

Concretely, the influenza subtype H3 test line of the signal pad of the first strip may be located at a distance of 0.7-1.1 cm from the lower end of the signal pad; the influenza type A test line of the signal pad of the first strip may be located at a distance of 1.1-1.5 cm from the lower end of the signal pad; the influenza type B test line of the signal pad of the first strip may be located at a distance of 1.5-1.9 cm from the lower end of the signal pad; and the mouse antibody C test line of the signal pad of the first strip may be located at a distance of 1.9-2.3 cm from the lower end of the signal pad. In addition, the influenza subtype H1 test line of the signal pad of the second strip may be located at a distance of 0.6-1.2 cm from the lower end of the signal pad; the influenza subtype H5 test line of the signal pad of the second strip may be located at a distance of 1.2-1.8 cm from the lower end of the signal pad; and the mouse antibody C test line of the signal pad of the second strip may be located at a distance of 1.8-2.4 cm from the lower end of the signal pad. However, the scope of the present invention is not limited thereto.

More concretely, the influenza subtype H3 test line of the signal pad of the first strip may be located at a distance of 0.9 cm from the lower end of the signal pad; the influenza type A test line of the signal pad of the first strip may be located at a distance of 1.3 cm from the lower end of the signal pad; the influenza type B test line of the signal pad of the first strip may be located at a distance of 2.1 cm from the lower end of the signal pad; and the mouse antibody C test line of the signal pad of the first strip may be located at a distance of 2.1 cm from the lower end of the signal pad. In addition, the influenza subtype H1 test line of the signal pad of the second strip may be located at a distance of 0.9 cm from the lower end of the signal pad; the influenza subtype H5 test line of the signal pad of the second strip may be located at a distance of 1.5 cm from the lower end of the signal pad; and the mouse antibody C test line of the signal pad of the second strip may be located at a distance of 2.1 cm from the lower end of the signal pad.

As used herein, "C" in "mouse antibody C" means a control that is a mouse antibody used to confirm the development of the sample.

In an example of the present invention, in the first strip, an influenza subtype H3 test line, an influenza type A test line, an influenza type B test line and a mouse antibody C test line were fixed in this order from the side close to the sample pad, and in the second strip, an influenza subtype H1 test line, an influenza subtype H5 test line and a mouse antibody C test line were fixed in this order from the side close to the sample pad, such that the cross-reaction of the antibody is avoided.

As found in the examples of the present invention, a positive signal for subtype H5 was detected in a reaction for detecting influenza type A, while no positive signal for other influenza types was detected in a reaction for detecting influenza subtype H5. For this reason, antibodies for detection of influenza type A and subtype H5 were placed in different strips in order to avoid the cross-reaction. In addition, it could be found that the influenza detection kit according to the present invention has high sensitivity and specificity to particularly subtype H5.

In another aspect, the present invention is directed to a method of detecting influenza using the multi-influenza detection kit of the present invention comprising monoclonal antibodies.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Preparation of Colloidal Gold 1-1: Preparation of Colloidal Gold

Colloidal gold was prepared through reducing $HAuCl_4$ with citrate. Specifically, one neck of a 10-liter three neck-flask mounted on a heating mantle was opened, and 1.98 L of triple-distilled water was carefully added to the flask through the opened neck, and then 0.4 mL of 5% gold chloride was added thereto and heated to 95° C. with stirring. At this time, the stirring was performed at moderate speed. When stock solution was used, it was well stirred after completely dissolved, because it had been stored in a frozen state. Also, gold chloride was weighed using a plastic spatula, because it would be immediately oxidized upon contact with a metallic material. Evaporated steam was caught with a cooler connected to the flask so that the amount of the reaction solution was maintained at a constant level. At this time, the solution had a light yellow color.

When the solution reached a temperature of 95° C. or higher, the stirring speed was increased to the highest possible speed. Then, a previously prepared mixture comprising 20 mL of 5% sodium citrate solution, 0.1 mL of 25 mM $K_2CO_3$ and 0.1 mL of 1% tannic acid was rapidly injected into the flask using a syringe or a pipette. The opened neck was very hot, and thus care was taken, and the mixture was added as fast as possible in order to prevent the loss of steam. The color of the reaction solution immediately turned black, and then turned red, which became more intense with the passage of time and then stabilized as a purple color (wine color). Then, the stirring speed was reduced, and the solution was further stirred for about 20 minutes, after which the heating was stopped.

Figure 2:
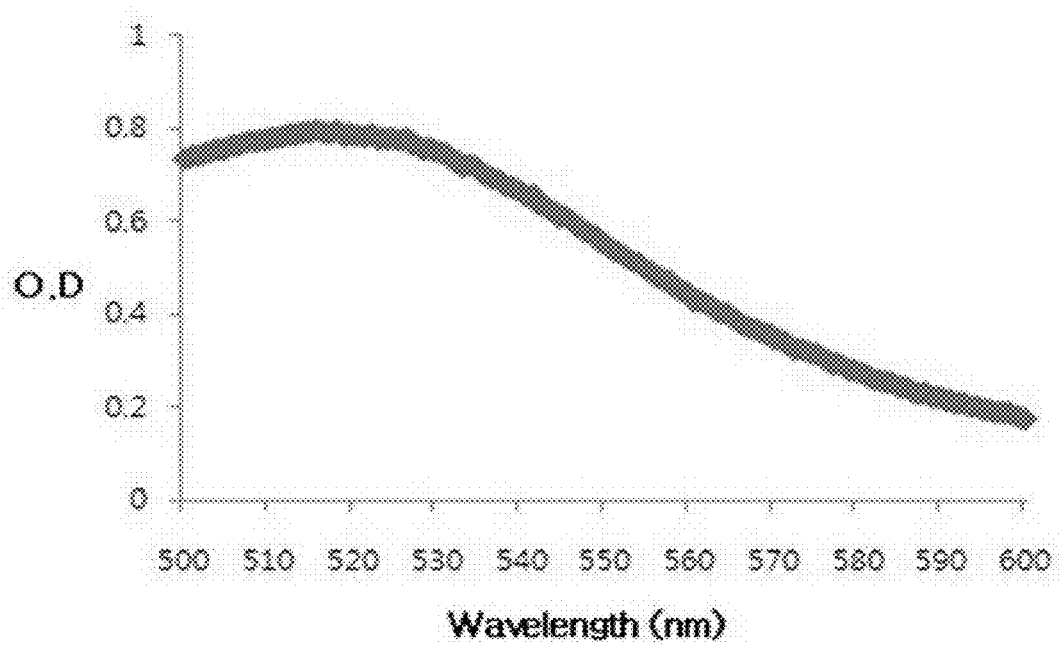
FIG. 2 shows the optical density (O.D.) of prepared colloidal gold particles as a function of wavelength.

Finally, after the solution had been cooled, it was scanned in a spectrophotometer at a wavelength of 500-600 nm. As a result, a peak was formed at 520 nm corresponding to an O.D. value of 0.8 (FIG. 2).

1-2: Caution in Preparation of Colloidal Gold $HAuCl_4$ should be handled with a non-metallic device, and a device used in the preparation of a colloidal gold solution should be washed with a non-metallic washer. In addition, the rotational speed of an impeller is important during an addition of a $HAuCl_4$ solution, and the $HAuCl_4$ solution should be added at a time as fast as possible. This is because the reaction is stopped when the rate of addition of the solution is low, and in this case, a change in color from dark blue does not occur. Also, the gold solution should be handled using a container treated with deionized water (DIW). In addition, the gold solution should be stored in a brown bottle in a dark place. Water that is used in this experiment is triple-distilled water, thus does not need to be sterilized, but should be filtered through filter paper having a pore size of 0.2 μm so that particle materials other than gold particles are not incorporated into the gold solution.

Example 2

Preparation of Antibody-colloidal Gold Conjugate 2-1: Screening and Purification of Antibody for Detection of Influenza Subtype H1

Antibodies specific for influenza type A, type B, subtype H3 and subtype H5 were purchased, and an antibody specific for subtype H1 was prepared by the present inventors.

In order to screen an antibody for detecting influenza virus subtype H1, an antibody pool was prepared by immunization with the 2009 swine influenza antigen using a hybridoma cell line preparation method (Kohler, G. and Milstein, C., 1975; Kozbar et al. 1983) known in the art. In brief, 6-8-week-old mice were immunized with swine influenza virus by intraperitoneal injection, and the spleens were extracted. Single cells were obtained from the spleens and incubated with myeloma cells to prepare a hybridoma cell line. The prepared hybridoma cell line was repeatedly cloned until a stable monoclonal cell line would be obtained, thereby preparing a hybridoma cell line that produces monoclonal antibodies. Among antibodies produced in the hybridoma cell line, antibodies having affinity for influenza virus subtype H1 were screened.

To screen an antibody for detecting influenza virus subtype H1 was screened by an ELISA method was used. A standard antibody for SRID (A/Brisbane/59/2007 (IVR-148); NIBSC, Lot No. 10/120) was used as a capture antibody, and a sample supernatant prepared by infecting MDCK cells with one kind of influenza virus (A/Brisbane/59/2007 (IVR-148)) was used as an antigen.

The standard antibody for SRID and the culture supernatant infected with IVR-148 were sequentially coated on a 96-well plate which was then treated with each antibody of an influenza antibody pool to thereby screen antibodies having affinity for IVR-148 virus. Next, each of the antibodies was purified by the IgG purification method known in the art in order to use the antibodies in the establishment of second screening and ELISA conditions.

After the antibodies were purified, SF587 and SF757 Fab fragments showing high binding affinity for influenza virus subtype H1 protein were analyzed for the amino acid sequences of their variable light chain and variable heavy chain (Table 1).

TABLE 1

Amino acid sequences of SF587 and SF757 antibodies

| Antibodies | | Amino acid sequences | SEQ ID NO: |
|---|---|---|---|
| SF587 | Variable heavy chain | VQLQQSGGGVVQPGGSLRLSCAASGFTFSDYDMSW IRQAPGKGLEWVSGILGGGERSYYNDSVKGRFTIS RDNSRKTLYLQMNSLRAEDTAVYYCARHGSSGYVD YGMDYWGQGTTVTVSS | SEQ ID NO: 1 |
| | Variable light chain | DIVLTQSPSFLSASVGDRVTITCRASQGIGDNLGW YQQKPGKAPKRLIYGVSTLDSGVPSRFSGSGSGTE FTLTINSLQPEDFATYYCLQHSNYPMYTFGQGTKL EIKR | SEQ ID NO: 2 |

TABLE 1-continued

Amino acid sequences of SF587 and SF757 antibodies

| Antibodies | | Amino acid sequences | SEQ ID NO: |
|---|---|---|---|
| SF757 | Variable heavy chain | VKLQESGGGVVQPGGSLRLSCAASGFTFSDYDMSW IRQAPGKGLEWVSGILGGSERSYYRDSVKGRSTIS RDNSRKTLYLQMNSLRAEDTAVYYCARHSWGAYVQ YGMDVWGQGTTVTVSS | SEQ ID NO: 3 |
| | Variable light chain | DIQMTQSPASLAVSPGQRATITCRASESVSNYGIN FINWFQQKPGQPPKLLIYTASNKGTGVPARFSGSG SGTDFTLTINPVEAEDTANYFCQQTKEVPYTFGGG TKLEIKR | SEQ ID NO: 4 |

(Underlined and bold portions indicate CDR regions).

2-2: Preparation of Antibody-colloidal Gold Conjugate

An antibody-colloidal gold conjugate was prepared in the following manner. First, 40 nm gold colloid was adjusted to pH 8.0 suitable for conjugation by adding 0.1M carbonate buffer thereto. Then, a monoclonal antibody that binds specifically to each of influenza H1, H3, H5, A and B was diluted with 10 mM borate buffer to a concentration of 0.1 mg/mL. Then, 100 μL of the antibody solution was added to 1 mL of the colloidal gold solution at a concentration of 0.1 mg/mL and reacted with mild shaking for 30 minutes. After 30 minutes of reaction, 100 μL of 10% BSA (bovine serum albumin) was added to the antibody-colloidal gold solution to a final concentration of 1% and incubated with mild shaking for 30 minutes.

To recover the formed antibody-colloidal gold conjugate, the solution was centrifuged at 13,000 rpm at 4° C. for 5 minutes. Then, 1 mL of the supernatant was removed, and the precipitate (antibody-colloidal conjugate) was resuspended in the remaining supernatant and collected in one tube, and 1 mL of 1% BSA/10 mM borate was added thereto, followed by centrifugation at 13,000 rpm at 4° C. for 5 minutes. Finally, the supernatant was completely removed, and the precipitate (antibody-colloidal conjugate) was rehydrated with 50 μL of 1% BSA/10 mM borate and concentrated at 20×. As a result, an antibody-colloidal conjugate could be obtained.

Example 3

Fabrication and Assembly of First Strip and Second Strip

3-1: Fabrication of Signal Pad for Each of First Strip and Second Strip

In order to establish a desired detectable antibody concentration and immobilize the antibody onto a signal pad by a physical adsorption method, monoclonal antibodies that bind specifically to influenza subtype H3, type A and type B were drawn as lines at distances of 0.9 cm, 1.3 cm and 1.7 cm, respectively, from the lower end of a signal pad of a first strip by use of a dispenser. Also, as a control for confirming the upward development of a sample, an antibody that binds specifically to mouse antibody was drawn as a line at a distance of 2.1 cm from the lower end of the signal pad by use of a dispenser. Then, the antibodies were incubated overnight at 37° C. to thereby be fixed to the signal pad.

Similarly, monoclonal antibodies that bind specifically to influenza subtypes H1 and H5 were drawn as lines at distances of 0.9 cm and 1.5 cm, respectively, from the lower end of a signal pad of a second strip by use of a dispenser. Also, as a control for confirming the upward development of a sample, an antibody that binds specifically to mouse antibody was drawn as a line at a distance of 2.1 cm from the lower end of the signal pad of the second strip by use of a dispenser. Then, the antibodies were incubated overnight at 37° C. to be fixed to the signal pad.

The kinds of monoclonal antibodies, which are fixed to the signal pads and bind specifically to influenza types, are shown in Table 2 below.

TABLE 2

Monoclonal antibodies fixed to signal pads

| Name | Sources of supply | Catalogue Number |
|---|---|---|
| H1 | In-house produced | — |
| H3 | Centers for Disease Control and Prevention | NCCP. 76024 |
| H5 | Hytest | 3H5N-15A6 |
| A | Biospacific | A60010044P |
| B | Fitzgerald | 10-I55B |

3-2: Fabrication of Conjugate Pad for Each of First Strip and Second Strip

To make a conjugate pad comprising an antibody-colloidal gold conjugate, a soaking method of completely soaking a pad in a conjugate solution was used. In order to make a conjugate pad for a first strip, a conjugate obtained by conjugating 40 nm gold colloid to a monoclonal antibody that binds specifically to each of influenza subtype H3, type A and type B was mixed with trehalose to a final concentration of 5%, and a conjugate pad for a first strip was soaked with the mixture, followed by freeze-drying for 1 hour, thereby depositing the antibody-colloidal gold conjugate on the conjugate pad.

In order to make a conjugate pad for a second strip, a conjugate obtained by conjugating 40 nm gold colloid to a monoclonal antibody that binds specifically to each of influenza subtype H1 and H5 was mixed with trehalose to a final concentration of 5%, and a conjugate pad for a second strip was soaked with the mixture, followed by freeze-drying for 1 hour, thereby depositing the antibody-colloidal gold conjugate on the conjugate pad.

The kinds of monoclonal antibodies, which are conjugated to colloidal gold top form conjugates and bind specifically to influenza types, are shown in Table 3 below.

TABLE 3

Monoclonal antibodies that are conjugated to colloidal gold to form conjugates

| Name | Sources of supply | Catalogue Number |
|---|---|---|
| H1 | In-house produced | — |
| H3 | Centers for Disease Control and Prevention | NCCP. 76024 |
| H5 | Hytest | 3H5N-15A6 |
| A | Medix | 7307 SPTN-5 |
| B | Medix | 9901 SPTNE-10 |

3-3: Assembly of First Strip and Second Strip

Figure 3:
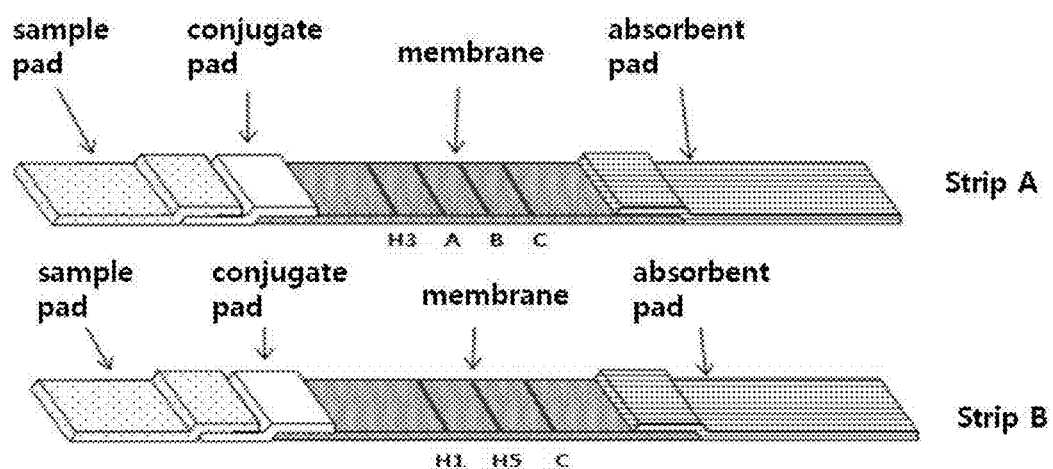
FIG. 3 is a schematic view of a multi-influenza antigen diagnosis system.
Figure 4:
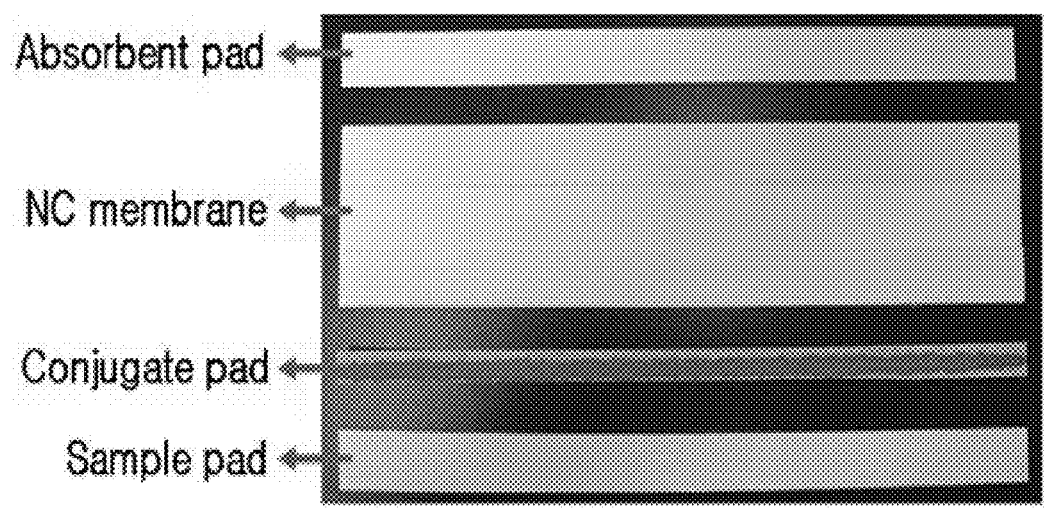
FIG. 4 shows the configuration of a strip comprising a sample pad, a conjugate pad, a NC membrane (signal pad) and an absorbent pad.

Each of the first strip and the second strip was composed of an absorbent pad, a signal pad, a conjugate pad and a sample pad. The conjugate pad was attached to the lower end of the signal pad, and the sample pad was attached onto the attached conjugate pad. The absorbent pad was attached to the upper end of the signal pad, thereby assembling each of the strips (FIGS. 3 and 4). Each of the assembled strips was accurately cut at intervals of 3.9 mm using a cutter, and the cut strips were assembled with a cassette (FIG. 5) so that the portion comprising the conjugate pad and the sample pad would be exposed. The first strip and the second strip were disposed in parallel so that their long axes were parallel to each other.

Example 4

Sensitivities at various antibody concentrations

Figure 6B:
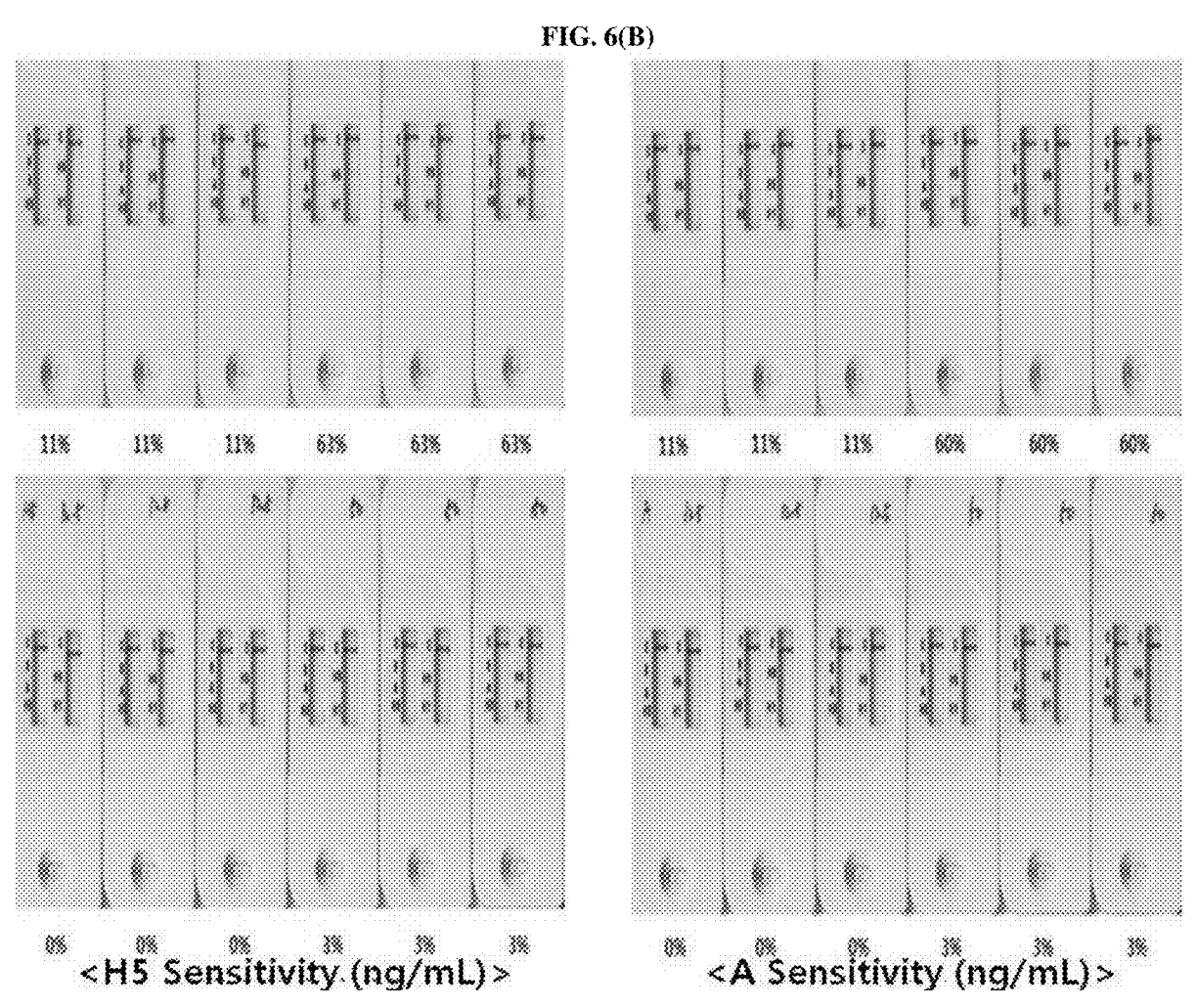
Figure 6C:
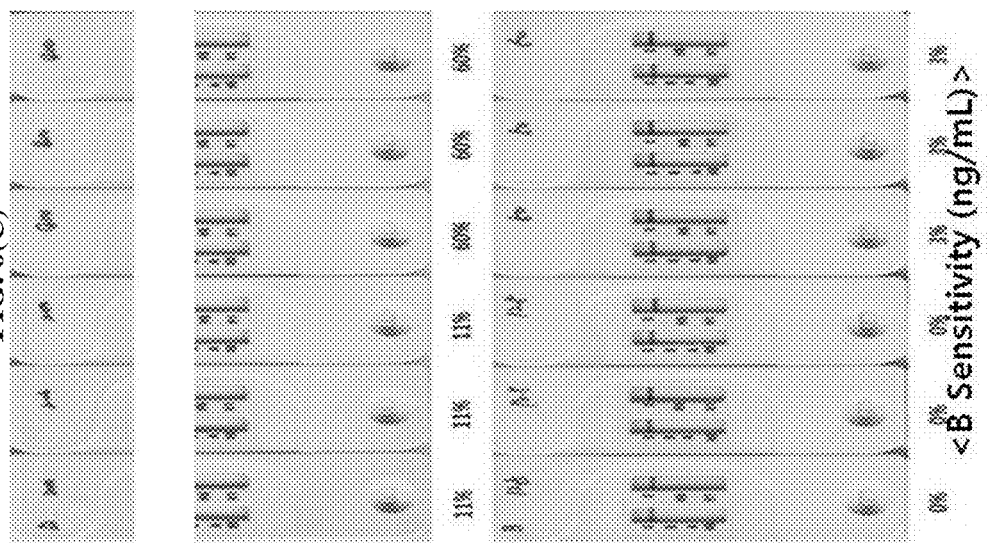

Each of standard antigens (H1, H3, H5, A and B) was diluted with a sample extract, and 180 μL of the dilution was added to the sample inlet of the assembled strip and allowed to stand for 15 minutes, after which the observation of signals caused by antigen-antibody reactions was performed. The experiment was performed at varying concentrations of H1, H3, H5, A and B antigens, and as a result, signals were observed at concentrations of up to 50 ng/mL (FIGS. 6(A), 6(B), and 6(C)).

Example 5

Sensitivity and Specificity of GENEDIA® Multi-Influenza Antigen Rapid Test (Green Cross Medical Science Corp.) Rapid Diagnostic Reagent It has been reported to date that sensitivities of influenza detection reagents developed in Korea vary between 31.3 to 91.4%.

In this example, GENEDIA® multi-influenza antigen rapid test (Green Cross Medical Science Corp), the commercialized influenza detection kit of the present invention which enables the identification of subtypes, was compared with various rapid antigen tests developed in Korea and other countries and a PCR test known as a confirmatory test for influenza to evaluate the performance thereof, and was also compared with the performance of foreign products that have been widely used.

Table 4 below shows a comparison of sensitivity to influenza types A and B between GENEDIA® multi-influenza antigen rapid test (Green Cross Medical Science Corp) and the reagents of other companies. As can be seen therein, the sensitivity of GENEDIA® multi-influenza antigen rapid test (Green Cross Medical Science Corp) rapid diagnostic reagent was about 15% higher than those of currently commercially available products (54.22% on average).

TABLE 4

Comparison of influenza detection sensitivity between GENEDIA ® multi-influenza antigen rapid test (Green Cross Medical Science Corp) and influenza diagnostic reagents of other companies

| Real-time PCR | Rapid diagnostic kit | | | |
|---|---|---|---|---|
| Seegene | SD | Humasis | Alere | Green Cross MS |
| Anyplex™ II RV16 Detection Assay (n) | Influenza Ag A/B/A (H1N1/2009) (n) | Influenza A/B Antigen Test (n) | BinaxNOW A&B Card (n) | GENEDIA Multi Influenza Ag Rapid Test (n) |
| Influenza A (75) | Influenza A (40/75) | Influenza A (31/75) Influenza A&B (1/75) | Influenza A (42/75) | Influenza A (55/75) |
| Influenza B (75) | Influenza B (49/75) | Influenza B (44/75) Influenza A&B (1/75) | Influenza B (38/75) Influenza A&B (5/75) | Influenza B (49/75) Influenza A&B (1/75) |
| Negative (100) | Negative (100/100) | Negative (100/100) | Negative (100/100) | Negative (99/100) Influenza A (1/100) |
| | sensitivity 59.33% (A 53.33%, B 65.33%) specificity 100% | sensitivity 50.00% (A 41.33%, B 58.67%) specificity 100% | sensitivity 53.33% (A 56.00%, B 50.67%) specificity 100% | sensitivity 69.33% (A 73.33%, B 65.33%) specificity 99% | n = number of samples

Table 5 below shows a comparison of sensitivity to the subtypes of influenza A. As can be seen therein, the H1 sensitivity of GENEDIA® multi-influenza antigen rapid test (Green Cross Medical Science Corp) was 65.38%, which was higher than that of Influenza Ag A/B/A (H1N1/2009) (SD, 26.92%), and the H3 sensitivity thereof was as good as 70.83%, even though it was not comparable with other product because there was no commercial product for H1. In addition, the H1 and H3 sensitivities of GENEDIA® multi-influenza antigen rapid test (Green Cross Medical Science Corp) were as good as 99.32% and 98.41%, respectively.

TABLE 5

Comparison of influenza subtype detection sensitivity between GENEDIA ® multi-influenza antigen rapid test (Green Cross Medical Science Corp) and diagnostic kits of other company

| Reverse Transcriptase PCR | Rapid diagnostic kit | |
|---|---|---|
| Seegene | SD | Green Cross MS |
| Seeplex Influenza A/B Onestep Typing Influenza A/H1 (26) | Influenza Ag A/B/A (H1N1/2009) (n) Influenza A/H1 (7/26) | GENEDIA Multi Influenza Ag Rapid Test (n) Influenza A/H1 (15/26) Influenza H1 (2/26) Influenza A/H3 (1/26) |
| Influenza A/H3 (48) | Test is impossible (There is currently no | Influenza A/H3 (33/48) Influenza A/H1 |

TABLE 5-continued

Comparison of influenza subtype detection sensitivity between GENEDIA® multi-influenza antigen rapid test (Green Cross Medical Science Corp) and diagnostic kits of other company

| Reverse Transcriptase PCR | Rapid diagnostic kit | |
|---|---|---|
| Seegene | SD | Green Cross MS |
| | commercially available raid product) | (2/48) Influenza H3 (1/48) |
| Negative (100) | Negative (100/100) | Negative (99/100) Influenza A/H3 (1/100) |
| | H1 sensitivity 26.92% | H1 sensitivity 65.38% (17/26) specificity 99.32% (147/148) H3 sensitivity 70.83% (34/48) specificity 98.41% (124/126) | n = number of samples

Example 6

Evaluation of Clinical Usefulness of GENEDIA® Multi-Influenza Antigen Rapid Test Kit for Influenza H5 Antigen Test 6-1: Sensitivity of Diagnostic Kit for Detection of Subtype H5

In order to examine the detection limit of the inventive kit for subtype H5 of avian influenza virus, a sensitivity test for two H5 subtypes (H5N3 and H5N2) was performed. The sensitivity test was performed by comparison of hemagglutinating units (HA units). Specifically, subtype H5N3 or H5N2 influenza virus containing 128 HA units was diluted two-fold serially from 1/2 to 1/256 or from 1/4 to 1/128 and allowed to react with the kit.

Figure 7:
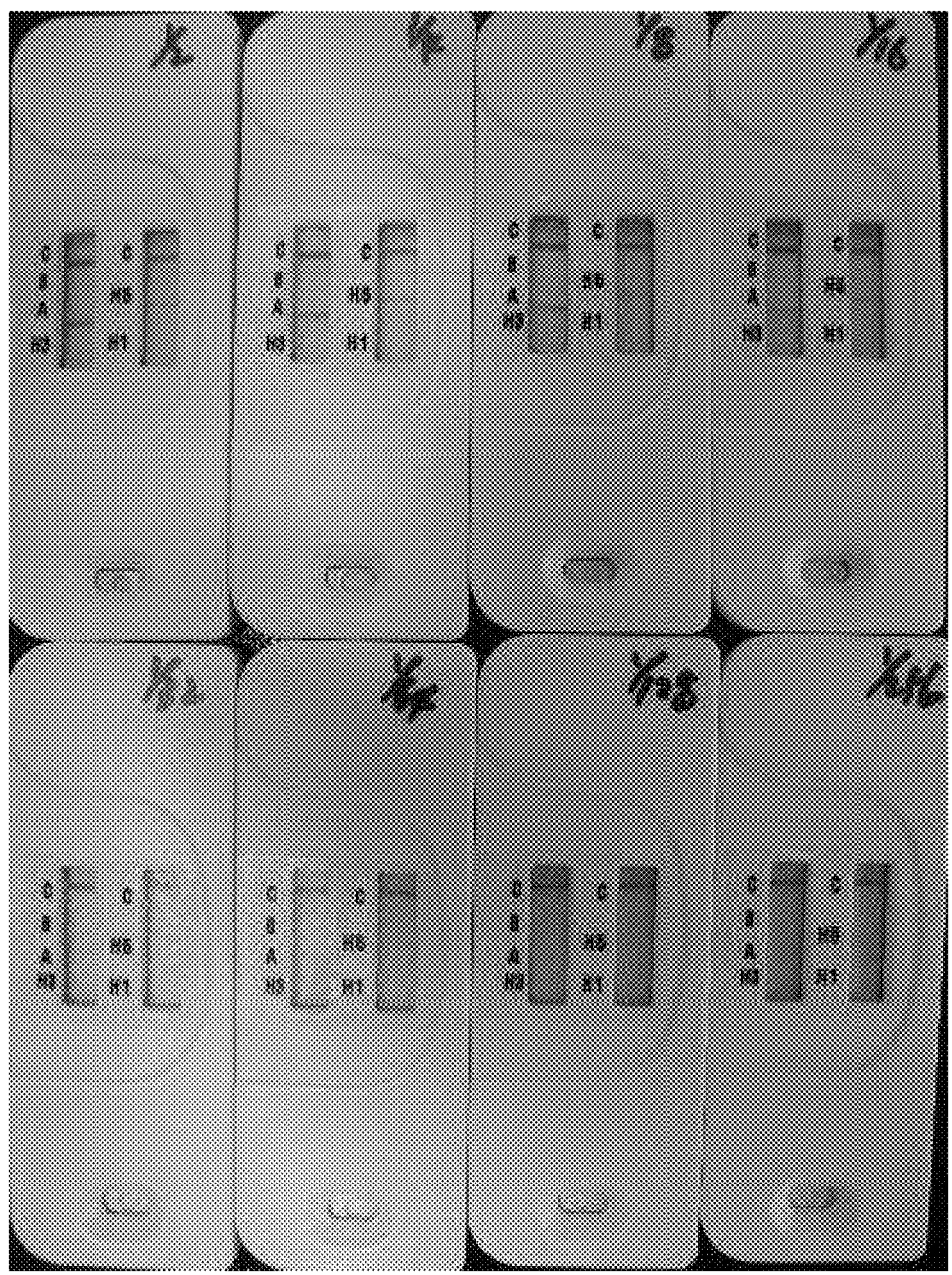
FIG. 7 depicts photographs of influenza detection kits, which show the results of testing the detection limit of subtype H5N3 virus at various dilution factors of the virus.

The results of the test performed using subtype H5N3 virus indicated that, in the reaction for detecting subtype H influenza virus, the kit of the present invention was negative at a virus concentration of 1 HA unit or less, but was positive at a virus concentration of 2 HA units or more (Table 6 and FIG. 7). Also, in the reaction for detecting type A influenza virus, the kit was positive at a virus concentration of 2 HA units or more, similar to the results in the subtype H detection test. However, in the reaction for detecting influenza type B virus and the reaction for detecting subtypes H1 and H3, the kit was negative even at a virus concentration of 64 HA units.

TABLE 6

Test for detection limit of diagnostic kit for subtype H5 detection (results for test performed using subtype H5N3 virus)

| | | Virus concentration | | | | | | | |
|---|---|---|---|---|---|---|---|---|---|
| | | Dilution factor | | | | | | | |
| | | 1/2 | 1/4 | 1/8 | 1/16 | 1/32 | 1/64 | 1/128 | 1/256 |
| Test results | HA units | 64 | 32 | 16 | 8 | 4 | 2 | 1 | 0.5 |
| | A | + | + | + | + | + | + | – | – |

TABLE 6-continued

Test for detection limit of diagnostic kit for subtype H5 detection (results for test performed using subtype H5N3 virus)

| | Virus concentration | | | | | | | |
|---|---|---|---|---|---|---|---|---|
| | Dilution factor | | | | | | | |
| | 1/2 | 1/4 | 1/8 | 1/16 | 1/32 | 1/64 | 1/128 | 1/256 |
| B | – | – | – | – | – | – | – | – |
| H1 | – | – | – | – | – | – | – | – |
| H3 | – | – | – | – | – | – | – | – |
| H5 | + | + | + | + | + | + | – | – |

Figure 8:
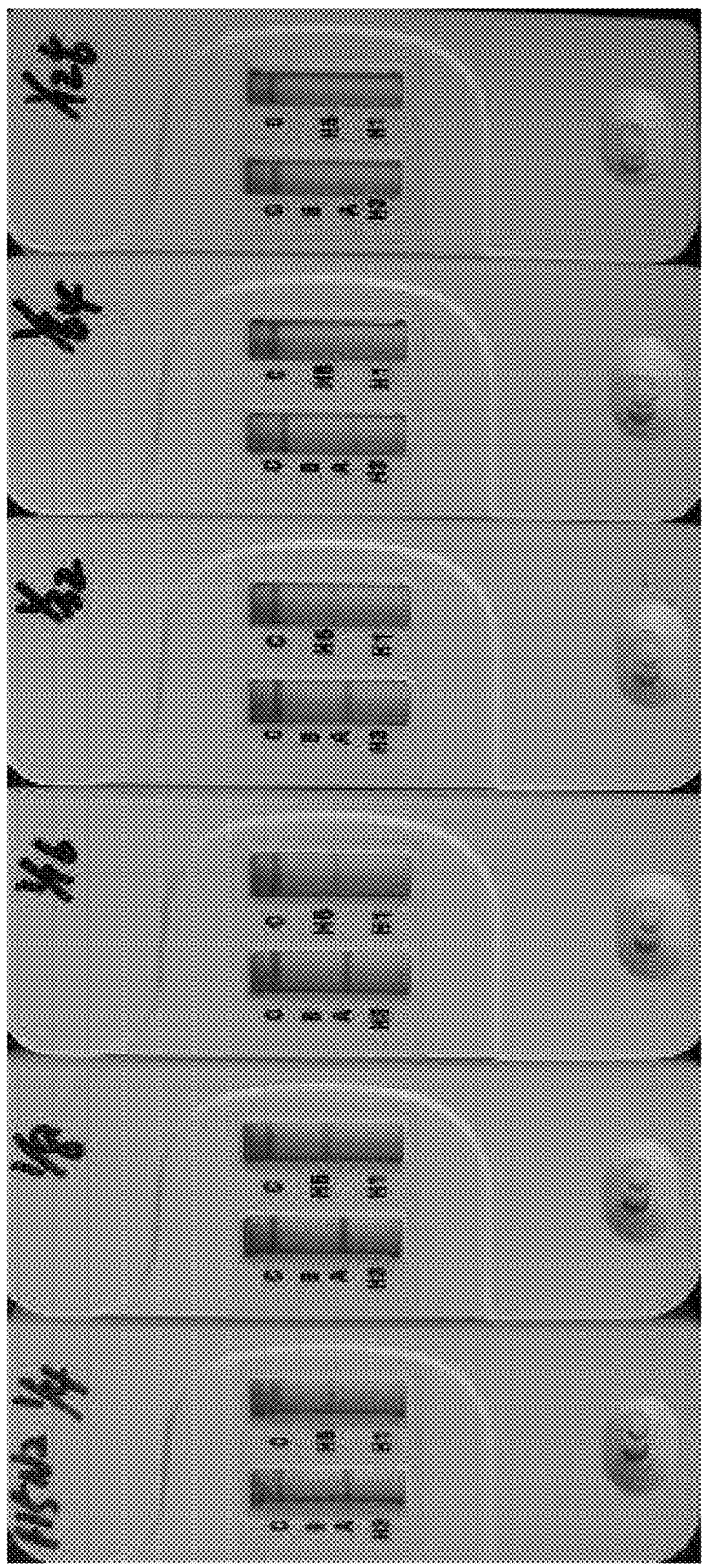
FIG. 8 depicts photographs of influenza detection kits, which show the results of testing the detection limit of subtype H5N2 virus at various dilution factors of the virus.
Figure 9A:
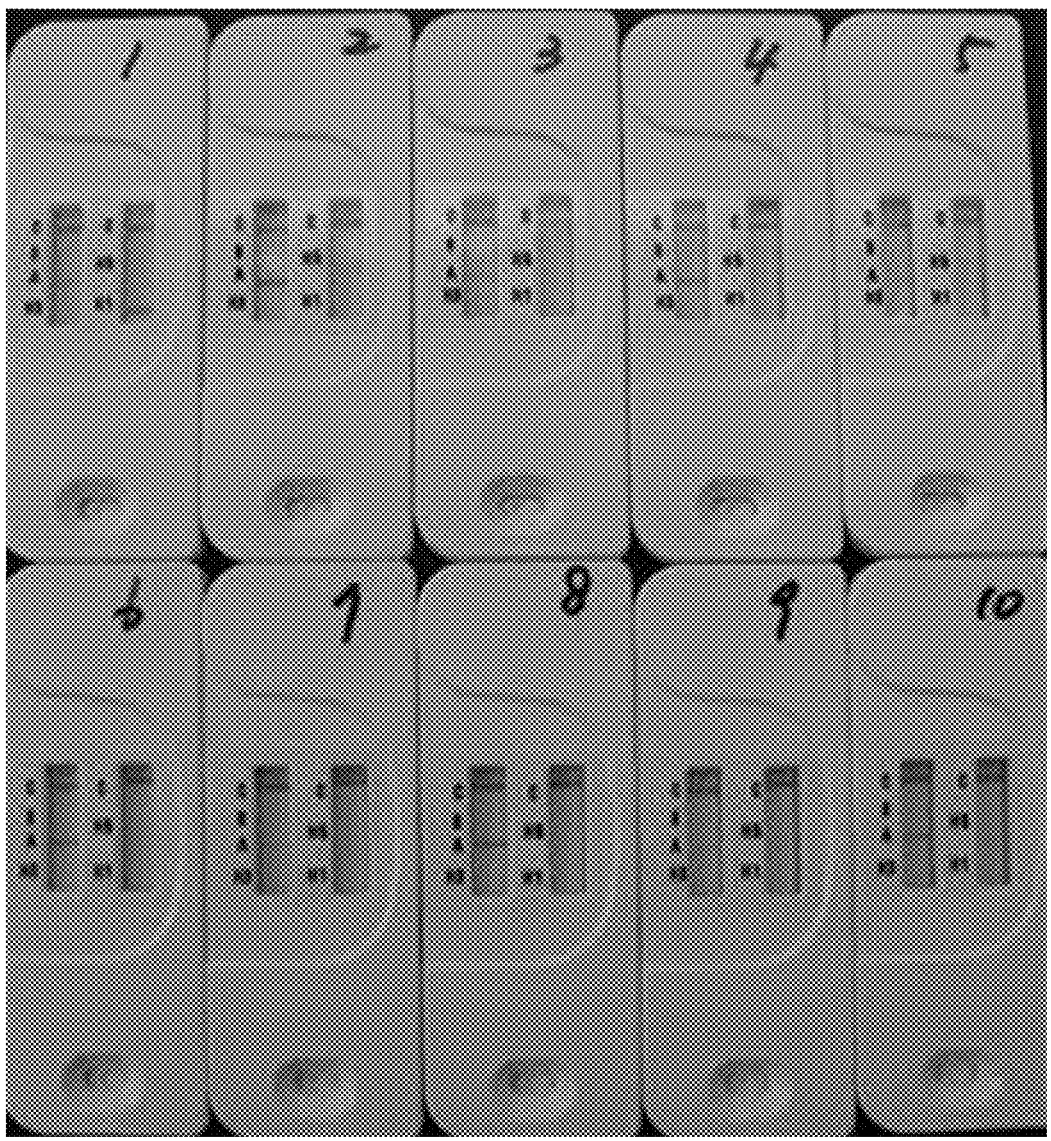
FIGS. 9(A)-9(E) depict photographs of influenza detection kits, which show the results of testing the cross-reactions of a subtype H5 detection kit with various subtypes.
Figure 9B:
Figure 9C:
Figure 9D:
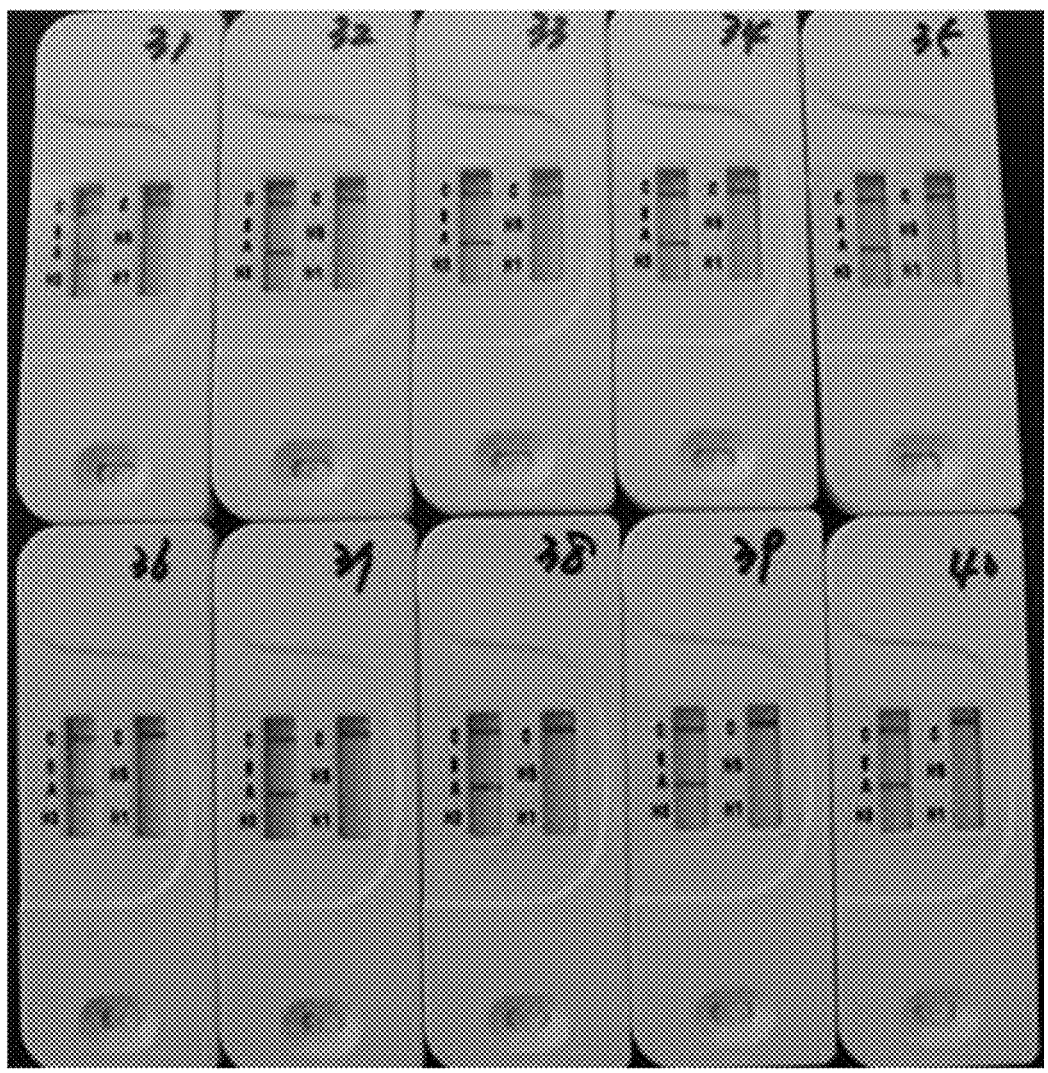
Figure 9E:
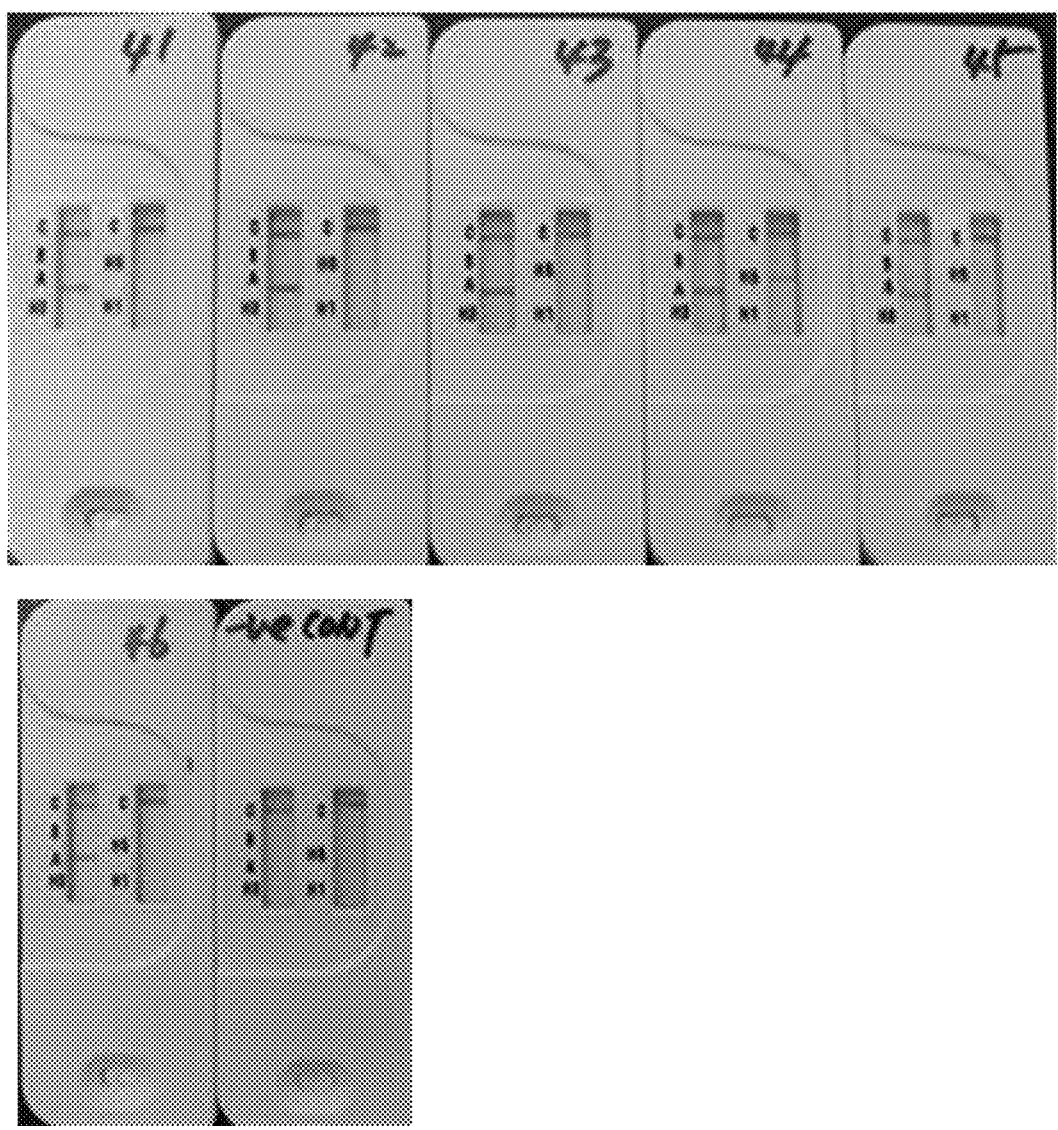

The results of the test performed using subtype H5N2 virus were also similar to the results of the test performed using subtype H5N3 influenza virus. Specifically, the results of the test performed using subtype H5N2 influenza virus indicated that, in the reaction for detecting subtype H influenza virus, the kit of the present invention was positive at a virus concentration of 2 HA units or more. Also, in the reaction for detecting type A influenza virus, the kit of the present invention was positive at a virus concentration of 2 HA units or higher, similar to the results of the subtype H detection test (Table 7 and FIG. 8). However, in the reaction for detecting type B influenza virus and the reaction for detecting subtypes H1 and H3, the kit of the present invention was negative even at a virus concentration of 64 HA units.

TABLE 7

Test for detection limit of diagnostic kit for subtype H5 detection (results for test performed using subtype H5N2 virus)

| | | Virus concentration | | | | | | | |
|---|---|---|---|---|---|---|---|---|---|
| | | Dilution factor | | | | | | | |
| | | 1/2 | 1/4 | 1/8 | 1/16 | 1/32 | 1/64 | 1/128 | 1/256 |
| Test results | HA units | 64 | 32 | 16 | 8 | 4 | 2 | 1 | 0.5 |
| | A | + | + | + | + | + | + | – | – |
| | B | – | – | – | – | – | – | – | – |
| | H1 | – | – | – | – | – | – | – | – |
| | H3 | – | – | – | – | – | – | – | – |
| | H5 | + | + | + | + | + | + | – | – |

The results of the test for the subtype H5 detection limit indicated that the kit of the present invention was negative to both subtype H5N3 and H5N2 viruses at a virus concentration of 1 HA unit or less, but was positive at a virus concentration of 2 HA units or more. This suggests that all of the reactions of the kit of the present invention will be positive at a virus concentration of 2 HA units or more.

6-2: Examination of Cross-Reactions With Other H Subtypes of Influenza Virus

In order to examine whether the subtype H5 detection kit cross-reacts with other H subtypes of influenza virus, the reactivity of the kit with various subtypes of type A influenza virus was tested. In the test, 46 subtype influenza virus strains isolated from birds were used. Specifically, 46 strains of a total of eight H subtypes (H1 (2 strains), H4 (1 strain), H5 (6 strains), H6 (12 strains), H7 (12 strains), H9 (10 strains), H11 (2 strains) and H12 (1 strain)) were used. The viruses used in the test had a titer of about 16-64 HA units.

The results of the test indicated that, in the reactions for detecting H5 subtypes of influenza virus, the kit of the present invention was positive for a total of six H5 influenza virus subtypes (H5N2 (No. 2), H5N2 (No. 14), H5N3 (No.

20), H5N3 (No. 23), H5N2 (No. 33) and H5N3 (No. 44)), but did not react with other subtypes of influenza virus. In addition, in the reaction for detecting type A influenza virus, the kit of the present invention was positive for all subtypes of avian influenza virus used in the test. In the reaction for detecting H1 subtypes, the kit was positive for only subtypes H1N1 (No. 1) and H1N1 (No. 11) of H1, and did not react with other subtypes of virus. The above results indicated that the kit of the present invention reacted with only H5 subtypes among various subtypes of influenza virus, and did not cross-react with other subtypes of influenza virus, suggesting that the kit has specificity for H5 subtypes of influenza virus (Table 8 and FIGS. 9(A), 9(B), 9(C), 9(D), and 9(E)).

TABLE 8

Results of test for cross-reactions of subtype H5 detection kit with various subtypes

| Sample. No. | Influenza virus | Subtype | A | B | H1 | H3 | H5 |
|---|---|---|---|---|---|---|---|
| 1 | Yangpyeong 2-2 | H1N1 | + | − | + | − | − |
| 2 | Field-Chuncheon 10-F2 | H5N2 | + | − | − | − | + |
| 3 | Paju 3-5 | H6N8 | + | − | − | − | − |
| 4 | Field- Chuncheon 9-F2 | H6N?* | + | − | − | − | − |
| 5 | Kimpo 3-2 | H11N9 | + | − | − | − | − |
| 6 | Market-Songuri store-chicken TR, CT | H9N2 | + | − | − | − | − |
| 7 | Market-Songuri store-Korean Ogol chicken TR, CT | H9N2 | + | − | − | − | − |
| 8 | Market-Kwangjeok market- Korean Ogol chicken TR, CT | H9N2 | + | − | − | − | − |
| 9 | Market-KwangJeok market-Korean chicken TR, CT | H9N2 | + | − | − | − | − |
| 10 | Market-Duckpo store -duck TR | H9N2 | + | − | − | − | − |
| 11 | Market-Wasoo Market-chicken TR, CT | H9N2 | + | − | − | − | − |
| 12 | Field-Yongsori, Jeju 3-②-F2 | H1N1 | + | − | + | − | − |
| 13 | Field-Hadori, Jeju 3-②-F6 | H4N6 | + | − | − | − | − |
| 14 | Field-Yongsuri, Jeju 4-①-F1 | H5N2 | + | − | − | − | + |
| 15 | Field- Cheonghocho 4-①-F1 | H7N7 | + | − | − | − | − |
| 16 | Field- Cheonghocho 4-①-F2 | H7N7 | + | − | − | − | − |
| 17 | Field- Cheonghocho 10-③-F3 | H6N8 | + | − | − | − | − |
| 18 | Field- Cheonghocho 9-①-F2 | H12N5 | + | − | − | − | − |
| 19 | Field- Cheonghocho 9-①-F3 | H6N? | + | − | − | − | − |
| 20 | Field- Cheonghocho 10-③-F1 | H5N3 | + | − | − | − | + |
| 21 | Field-Gyeopo lake 12-②-F3 | H7N? | + | − | − | − | − |
| 22 | Field-Yongsuri, Jeju 2-②-F4 | H11N? | + | − | − | − | − |
| 23 | Field-Yongsuri, Jeju 12-②-F2 | H5N3 | + | − | − | − | + |
| 24 | Field-Tokyo reservoir 11-①-F2 | H6N? | + | − | − | − | − |
| 25 | Field-Tokyo reservoir 11-①-F3 | H6N? | + | − | − | − | − |
| 26 | Field-Tokyo reservoir 11-①-F4 | H6N? | + | − | − | − | − |
| 27 | Field-Hadori, Jeju 11-②-F1 | H6N? | + | − | − | − | − |
| 28 | Field-Hadori, Jeju 11-②-F2 | H6N? | + | − | − | − | − |
| 29 | Field-Hadori, Jeju 11-②-F4 | H6N? | + | − | − | − | − |
| 30 | Field-Hadori, Jeju 11-②-F6 | H6N? | + | − | − | − | − |
| 31 | Field-Yongsuri, Jeju 11-②-F4 | H7N1 | + | − | − | − | − |
| 32 | Field- Tokyo reservoir 11-①-F1 | H9N? | + | − | − | − | − |
| 33 | Field-Yongsuri, Jeju 12-①-F4 | H5N2 | + | − | − | − | − |
| 34 | Field- Cheonghocho 10-③-F3 | H9N? | + | − | − | − | − |
| 35 | Field-Yongsuri, Jeju-1-①-F5 | H7N? | + | − | − | − | − |
| 36 | Field-Hadori, Jeju-1-①F2 | H7N? | + | − | − | − | − |
| 37 | Field-Hadori, Jeju-1-①F3 | H7N? | + | − | − | − | − |
| 38 | Field-Yongsuri, Jeju-1-②F2 | H7N1 | + | − | − | − | − |
| 39 | Field-Hadori, Jeju-1-②F3 | H7N? | + | − | − | − | − |
| 40 | Field-Hadori, Jeju-1-②F5 | H7N? | + | − | − | − | − |
| 41 | Field-Yongsuri, Jeju 1-③-F3 | H7N1 | + | − | − | − | − |
| 42 | Field-Gyeongho lake 3-④-F2 | H7N? | + | − | − | − | − |
| 43 | House- Chuncheon 10-②-F1 | H6N2 | + | − | − | − | − |
| 44 | SYG06 | H5N3 | + | − | − | − | + |
| 45 | MS96 | H9N2 | + | − | − | − | − |
| 46 | 07033 CT | H9N2 | + | − | − | − | − |
| | Negative control | | − | − | − | − | − |

*? viruses whose subtypes were not accurately identified.

INDUSTRIAL APPLICABILITY

As described above, the multi-influenza detection kit comprising monoclonal antibodies according to the present invention can simultaneously detect influenza types A and B and subtypes H1, H3 and H5, and thus is useful for the rapid and highly sensitive on-site detection and diagnosis of influenza.

The invention claimed is:

1. A multi-influenza detection kit comprising a first strip and a second strip, wherein each of the first strip and the second strip comprises a sample pad, a conjugate pad, a signal pad, and an absorbent pad, wherein the conjugate pad and the signal pad of the first strip comprise a monoclonal antibody capable of binding specifically to influenza subtype H3, a monoclonal antibody capable of binding specifically to influenza type A, and a monoclonal antibody capable of binding specifically to influenza type B, wherein the conjugate pad and the signal pad of the second strip comprise a monoclonal antibody capable of binding specifically to influenza subtype H1 and a monoclonal antibody capable of binding specifically to influenza subtype H5, wherein the monoclonal antibody capable of binding specifically to influenza subtype H1 comprises (i) a heavy chain variable region comprising the amino acid sequence of SEQ ID NO:1 and a light chain variable region comprising the amino acid sequence of SEQ ID NO:2, or (ii) a heavy chain variable region comprising the amino acid sequence of SEQ ID NO:3 and a light chain variable region comprising the amino acid sequence of SEQ ID NO:4.

2. The multi-influenza detection kit of claim 1, wherein the monoclonal antibody capable of binding specifically to the influenza subtype H3 binds specifically to hemagglutinin of the influenza subtype H3, the monoclonal antibody capable of binding specifically to the influenza type A binds specifically to nucleoprotein of the influenza type A, and the monoclonal antibody capable of binding specifically to the influenza type B binds to nucleoprotein of the influenza type B, and the monoclonal antibody capable of binding specifically to the influenza subtype H1 binds specifically to hemagglutinin of the influenza subtype H1, and the monoclonal antibody capable of binding specifically to the influenza subtype H5 binds specifically to hemagglutinin of the influenza subtype H5.

3. The multi-influenza detection kit of claim 1, wherein a longitudinal axis of the first strip is arranged in parallel to a longitudinal axis of the second strip.

4. The multi-influenza detection kit of claim 1, wherein the conjugate pad of the first strip and the conjugate pad of the second strip each further comprise a label bound to the respective monoclonal antibodies contained therein, and the signal pad of the first strip and the signal pad of the second strip each comprise test lines in which the respective monoclonal antibodies contained therein are immobilized.

5. The multi-influenza detection kit of claim 4, wherein the label is colloidal gold.

6. The multi-influenza detection kit of claim 4, wherein the test lines of the signal pad of the first strip comprise an influenza subtype H3 test line comprising the monoclonal antibody capable of binding specifically to influenza subtype H3, an influenza type A test line comprising the monoclonal antibody capable of binding specifically to influenza type A, and an influenza type B test line comprising monoclonal antibody capable of binding specifically to influenza type B, which are arranged in this order from a side closest to the sample pad of the first strip, and wherein the test lines of the signal pad of the second strip comprise an influenza subtype H1 test line comprising the monoclonal antibody capable of binding specifically to influenza type H1 and an influenza subtype H5 test line comprising the monoclonal antibody capable of binding specifically to influenza type H5, which are arranged in this order from a side closest to the sample pad of the second strip.

7. The multi-influenza detection kit of claim 6, wherein the signal pad of each of the first strip and the second strip further comprises an antibody that binds specifically to a mouse antibody which is used as a control to confirm the development of the sample, and wherein the antibody that binds specifically to a mouse antibody is immobilized in a control test line on the signal pad of each of the first strip and the second strip.

8. The multi-influenza detection kit of claim 7, wherein the sample pad, the conjugate pad, the signal pad, and the absorbent pad of the first and the second strips are arranged along a longitudinal direction of the first and the second strips;

wherein the signal pad of the first strip and the signal pad of the second strip each have a first boundary and a second boundary which are perpendicular to the longitudinal direction and define the signal pad;

wherein the influenza subtype H3 test line of the signal pad of the first strip is located at a distance of 0.7-1.1 cm from the first boundary of the signal pad; the influenza type A test line of the signal pad of the first strip is located at a distance of 1.1-1.5 cm from the first boundary of the signal pad; the influenza type B test line of the signal pad of the first strip is located at a distance of 1.5-1.9 cm from of the signal pad; and the control test line of the signal pad of the first strip is located at a distance of 1.9-2.3 cm from the first boundary of the signal pad; and wherein the influenza subtype H1 test line of the signal pad of the second strip is located at a distance of 0.6-1.2 cm from the first boundary of the signal pad; the influenza subtype H5 test line of the signal pad of the second strip is located at a distance of 1.2-1.8 cm from the first boundary of the signal pad; and the control test line of the signal pad of the second strip is located at a distance of 1.8-2.4 cm from the first boundary of the signal pad.

9. A method of detecting influenza using the multi-influenza detection kit of claim 1.

10. A method of detecting influenza using the multi-influenza detection kit of claim 2.

11. A method of detecting influenza using the multi-influenza detection kit of claim 3.

12. A method of detecting influenza using the multi-influenza detection kit of claim 4.

13. A method of detecting influenza using the multi-influenza detection kit of claim 5.

14. A method of detecting influenza using the multi-influenza detection kit of claim 6.

15. A method of detecting influenza using the multi-influenza detection kit of claim 7.

16. A method of detecting influenza using the multi-influenza detection kit of claim 8.

* * * * *